United States Patent [19]

Yamasaki et al.

[11] Patent Number: 4,788,141
[45] Date of Patent: Nov. 29, 1988

[54] AUTOMATIC ANALYZER FOR GUANASE ACTIVITY

[75] Inventors: Seiichiro Yamasaki, Fukuoka; Setsuro Fujii, Kyoto; Isao Nakagawa, Sakai; Nobumoto Chikazawa, Nara; Toshiharu Muraoka, Nagaokakyo, all of Japan

[73] Assignee: Maruho Co., Ltd., Osaka, Japan

[21] Appl. No.: 78,009

[22] Filed: Jul. 24, 1987

Related U.S. Application Data

[63] Continuation of Ser. No. 749,263, Jun. 27, 1985, abandoned.

[30] Foreign Application Priority Data

Jul. 4, 1984 [JP] Japan .................. 59-139370

[51] Int. Cl.$^4$ .................. C12Q 1/34; G01N 35/04
[52] U.S. Cl. .................. 435/18; 422/64; 422/67; 435/25
[58] Field of Search .................. 435/18, 25; 422/63, 422/65, 67, 64

[56] References Cited

U.S. PATENT DOCUMENTS 4,451,433  5/1984  Yamashita et al. .................. 422/63
4,483,823  11/1984  Umetsu et al. .................. 422/63

FOREIGN PATENT DOCUMENTS

3133191    4/1982  Fed. Rep. of Germany ........ 422/64
55-121092  3/1982  Japan .................. 422/64
57-64616   4/1982  Japan .

Primary Examiner—Michael S. Marcus
Attorney, Agent, or Firm—Sandler & Greenblum

[57] ABSTRACT

An automatic analyzer comprising a plurality of sample containers for accommodating different blood samples individually, specific sample container moving means, a plurality of reagent containers for accommodating at least a reagent for an assay of guanase activity, a specific reagent container holding means, a plurality of reaction containers, specific reaction container moving means, specific sample pouring means, specific cleaning vessels, specific stirring means, specific measuring means, specific cleaning means, a specific analog-digital converter, specific counting-calculating means, a specific display means, and specific operation control means, so that the display means produces a signal for excluding the measured blood sample corresponding to a display value when the display value is above a predetermined reference value of guanase activity.

3 Claims, 4 Drawing Sheets

AUTOMATIC ANALYZER FOR GUANASE ACTIVITY

This application is a continuation of application Ser. No. 749,263, filed June 27, 1985, now abandoned.

BACKGROUND OF THE INVENTION

1. Field of the Invention

The present invention relates to an automatic analyzer of blood automatically analyzing blood samples for transfusions, and more particularly to an automatic assay system for screening blood samples to prevent or inhibit the onset of transfusional hepatitis.

2. Description of the Prior Art

The occurrence of transfusion-induced hepatitis is one of the difficult medical problems in recent years. Since this disease is epidemiologically in correlation with blood transfusion, the incidence of the disease tends to increase with the increase in the amount of transfusion due to the advance of surgery. The disease not only retards the recovery of the transfused patient but also produces a prolonged aftereffect on him, possibly enadngering his life, and hence posing a serious problem of the community.

Presently, the Japanese Red Cross Society, Blood Center screens out abnormal blood using alanine aminotransferase (hereinafter referred to as "GPT"), Wasserman reaction and HBs as indicators. In actuality, however, hepatitis postoperatively develops even from normal transfused blood which is up to 35 IU/liter in GPT and negative for the Wasserman reaction and for HBs, and a majority of such cases of hepatitis are of the non-A non-B type. Accordingly, to completely prevent the onset of postoperative hepatitis, natural transfusion blood needs to be replaced by packed blood preparations or artificial blood, but an artificial blood which is comparable to natural blood still remains to be developed as an actual problem. At present, therefore, natural blood is used at some risks, and it is imperative to develop a highly reliable method of screening transfusion blood to avoid the hazard of hepatitis.

In the course of our research on substances which are serviceable as indicators of non-A non-B type hepatitis, we checked a large number of blood samples for serum guanase activity and further statistically investigated the relation between this activity and the incidence of hepatitis to find a very good correlation therebetween. While guanase is an enzyme associated with the metabolism of purine bases, as is well known, the finding is of extreme interest regardless of how the variation in the amount of the enzyme is biochemically related to non-A non-B type hepatitis.

Figure 4:
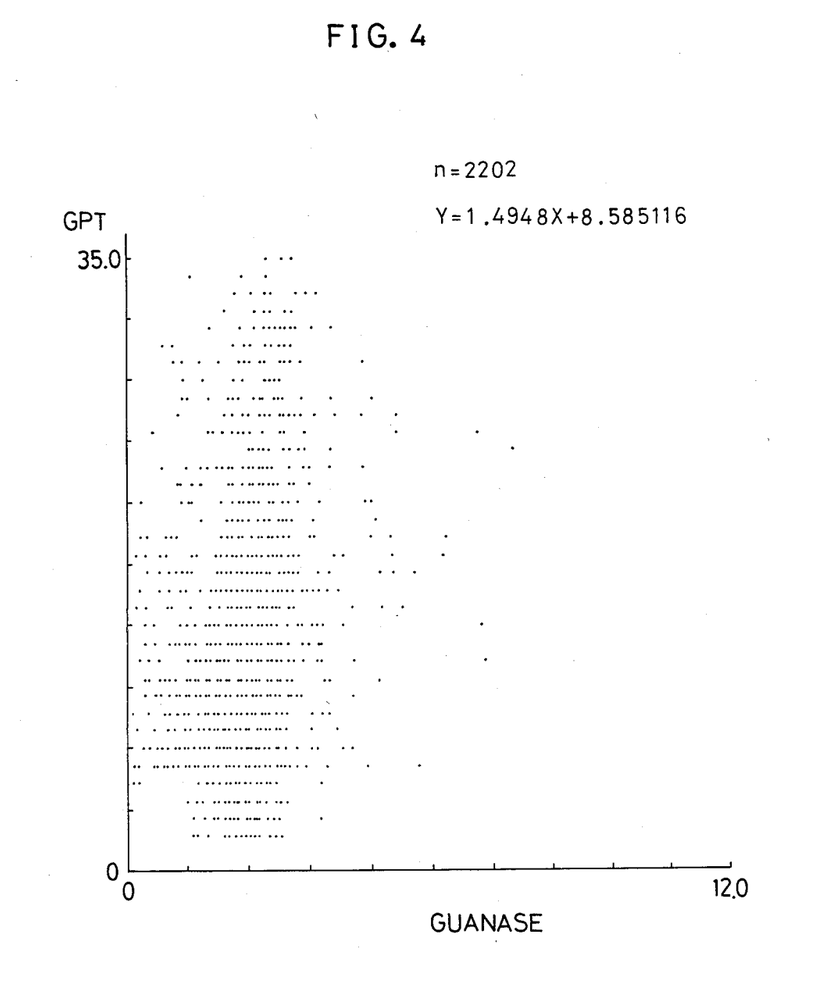
FIG. 4 is a graph generally showing the correlation between the GPT measurement and the guanase measurement.

On the other hand, we investigated the possible correlation between the guanase activity and the GPT activity which is usually used for screening normal blood. The investigation revealed little or no correlation between these activities (see FIG. 4). This indicates that the screening of transfusion blood with reference to the guanase activity has an epidemiological significance different from that of the conventional method.

Based on the above findings, we have already filed Published Unexamined Japanese patent application No. 64616/1982, finding that a manual method of assaying guanase by direct colorimetric determination of ammonia is useful especially for screening the blood for transfusions.

Stated more specifically, we checked samples of normal blood obtained from the Japanese Red Cross, Blood Center for guanase activity by the manual method, i.e. by reacting the serum guanase with 8-azaguanine as a substrate and colorimetrically determining the resulting ammonia by the indophenol reaction. The correlation between the guanase activity thus determined and the occurrence of hepatitis after blood transfusion was investigated based on the findings obtained after transfusions at two clinical institutions. Table 1 and Table 2 show the results.

TABLE 1

|  | Guanase activity (IU/L) | | |
| --- | --- | --- | --- |
|  | >2.6 | <2.5 | Total |
| Number of patients developing hepatitis | 9 | 13 | 22 |
| Number of patients without hepatitis | 5 | 89 | 94 |
| Total | 14 | 102 | 116 |
| Incidence of hepatitis (%) | 64.3 | 12.7 | |

$X^2 = 18.6 > (1, 0.001) = 10.83$
Significant difference at 0.1% level.

TABLE 2

|  | Guanase activity (IU/L) | | | |
| --- | --- | --- | --- | --- |
|  | Unchecked | >2.1 | <2.0 | Total |
| Number of patients developing hepatitis | 15 | 20 | 15 | 50 |
| Number of patients without hepatitis | 10 | 6 | 36 | 52 |
| Total | 25 | 26 | 51 | 102 |
| Incidence of hepatitis (%) | 60 | 76 | 29.4 | |

$X^2 = 17.5 > (2, 0.001) = 13.82$
Significant difference at 0.1% level.

The above tables reveal that the screening of the blood for transfusions according to guanase activity as a standard remarkably reduces the incidence of postoperative hepatitis. We further carried out research and found it most suitable for select blood with guanase activity of less than 2.9 IU/L by the above method.

However, the above screening method, which is practiced manually and requires a period of time for the indophenol reaction, has the drawback of being unable to check a large quantity of blood samples quickly and not amenable to automation. Accordingly it has been desired to provide automatic analysis method and apparatus for assaying and screening a large number of samples continuously and rapidly.

In this respect, various manual methods other than the foregoing are known for determining guanase activity, including some which appear relatively efficient, so that it will be useful to select such a method for automatic analysis. Nevertheless, what matters is whether there is a correlation between the manual method and the feasible automatic analysis method. For example, the manual method resorting to the indophenol reaction differs in substrate from the reaction rate assay or end point assay used for automatic analysis according to the present invention. Additionally, little has been reported as to an automatic assay of guanase activity by any method. It is therefore difficult to definitively conclude that the manual method and the automatic method are alike in the result to be achieved. In fact, it was not clear whether the reference value of 2.9 IU/L for the manual method could be the reference level for screening the blood by automatic analysis.

We have practiced a specific method of determination using a specific automatic analyzer to investigate the correlation between this method and the conventonal manual method and found a very good correlation between the two methods in respect of gunanase activity. We have further found that by this method thus conducted automatically, that blood can be screened rapidly with high reliability when a reference value of about 1.8 IU/L is used under specified conditions instead of the conventional value of 2.9 IU/L.

SUMMARY OF THE INVENTION

The main object of the present invention is to provide an automatic analyzer for screening a large quantity of blood samples for transfusion accurately at a high speed by improving the method without prior invention for automatic assay.

Stated more specifically, the present invention provides an automatic analyzer comprising a plurality of sample containers for accommodating different blood samples individually, sample container moving means for holding the sample containers as arranged in a row or rows with their open ends up and intermittently moving the sample containers in the direction of the row, a plurality of reagent containers for accommodating at least a reagent for an assay of guanase activity, a reagent container holding means for holding the reagent containers with their open ends up and maintaining the reagent containers at a predetermined temperature, a plurality of reaction containers, reaction container moving means for holding the reaction containers as arranged in a row or rows with their open ends up and intermittently moving the reaction containers in the direction of the row, a temperature controlled bath for maintaining the interior of the reaction containers at a constant temperature, sample-reagent pouring means having a pouring nozzle reciprocatingly movable in a direction from the sample container moving means or the reagent container holding means to the reaction container moving means and in a direction opposite to the direction for pouring a sample or reagent into each of the reaction containers, cleaning vessels for cleaning the pouring nozzle of the sample-reagent pouring means every time the sample or the reagent has been completely poured, stirring means for stirring the mixture of sample and reagent to be reacted and poured into the reaction container at a position forwardly of the sample-reagent pouring position in the direction of movement of the reaction container moving means, measuring means for colorimetrically measuring the absorbance of the reaction mixture at a position forwardly of the stirring means in the direction of movement of the reaction container moving means, cleaning means for cleaning the interior of the reaction container after the completion of the measurement at a position forwardly of the measuring means in the direction of movement of the reaction container, an analogdigital converter for converting a measurement signal output from the measuring means into a digital signal, counting-calculating means for counting and calculating the digital signal, display means for showing the calculated value as converted to a display signal, and operation control means for controlling the operation of the reaction container moving means, the sample-reagent pouring means, the cleaning means and the stirring means, the display means being adapted to produce a signal for excluding the measured blood sample corresponding to a display value when the display value is above a predetermined reference value of guanase activity.

The reference value of guanase activity is a specific value as measured with use of guanine and expressed in IU/L, i.e. in international units per liter of blood. One international unit is an amount of enzyme which produces the change of 1 micromole of the substrate during a period of 1 minute under a given condition.

According to the present invention, the above unit is determined based on a value measured at a temperature of 37° C. and at an optimum pH.

According to the invention, a large quantity of blood samples can be rapidly checked for guanase activity to reliably screen out the blood which causes hepatitis when infused.

DESCRIPTION OF THE PREFERRED EMBODIMENT

For the measurement with use of the system of the present invention, a fully accurate and highly sensitive method must be used.

Although various methods appear usable for measuring guanase activity, a shorter measuring cycle is required for each sample because a large number of blood samples are to be handled. Thus, the colorimetric method resorting to the indophenol reaction and the direct colorimetric determination of ammonia is in no way usable for automatic analysis. From such viewpoint, the following methods can be used for the automatic determination of guanase activity according to the present invention;

(i) Method wherein the ammonia resulting from the reaction of guanase with guanine as the substrate is determined based on a reduction of NADH in the presence of GLDH for the calculation of guanase activity, instead of resorting to the indophenol reaction.

(ii) Method wherein the xanthine resulting from the reaction of guanase with guanine as the substrate is directly determined with UV for the calculation of the activity.

(iii) Method comprising reacting xanthine oxidase with the xanthine obtained from the method (ii), reacting the resulting hydrogen peroxide with peroxidase, 3-methyl-2-benzothiazolinonehydrazine and a dialkylaniline and colorimetrically determining the amount of indamine pigment produced for calculation.

(iv) Method which comprises reacting xanthine oxidase and uricase with the xanthine obtained by the method (ii), reacting the resulting hydrogen peroxide with peroxidase, 3-methyl-2-benzothiazolinonehydrazine and a dialkylaniline and colorimetrically determining the amount of indamine dye formed, followed by calculation.

(v) Method wherein xanthine oxidase is reacted with the xanthine obtained by the method (ii), and the resulting uric acid is determined with UV, followed by calculation.

(vi) Method which comprises reacting milk-derived xanthine oxidase with the xanthine resulting from the method (ii), causing the resulting super-oxide radical to act on a color developing system (for example, of 1-methoxyphenazine sulfate and 2,2-di-p-nitrophenyl-5,5-diphenyl-3,3-(3,3-dimethoxy-4,4-diphenyl)ditetrazolium) and calculating the activity from the variation in the absorbance of the reaction mixture.

For the actual determination, end point assay, reaction rate assay and one point assay are usable.

However, our research has revealed the following.

(a) Reaction rate assays permit automatic analysis with increased accuracy and remarkably improved sensitivity when the method (vi) is practiced by (a) conducting the xanthine forming reaction in the presence of a nonionic surfactant, and (b) conducting the uric acid forming reaction in the presence of an electron transfer agent such as phenazine sulfate.

Principle of assay mPMS: 1-methoxyphenazine sulfate
NBT: 2,2-di-p-nitrophenyl-5,5-diphenyl-3,3-(3,3-dimethoxy-4,4-diphenyl)ditetrazolium (b) End point assays can be carried out rapidly, are suited to automatic analysis and achieve improved accuracy when the method (iv) is practiced by four divided steps, i.e. xanthine forming raction, hydrogen peroxide forming reaction in two stages and color developing reaction.

Principle of assay

MBTH: 3-methyl-2-benzothiazolinonehydrazone
DEA: N,N—diethylaniline

According to the present invention, a distinct correlation is observed between the result obtained by the manual method and the result achieved by the present automatic analyzer. Consequently, it has become possible to check a large quantity of blood samples for guanase activity at a high speed with use of the automatic analyzer. However, the problem is what guanase activity value (maximum value) is to be used as a standard or reference for acceptance or rejection. As is well known, the blood supply-demand situation in clinical institutions changes with time owing to the reason specific to each institution and to the variation in the amount of surgical operation necessitating transfusions, so that it is impossible to definitely determine a specific reference value (upper limit value). However, when the assay methods (a) and (b) are employed, it is suitable to set the reference to 1.8 IU per liter of blood, as measured at pH 8.0 with use of guanine as the substrate. (This value was determined from the correlation between the reaction rate assay method, as well as end point assay method, and the manual method disclosed in the foregoing Publication No. 64616/1982 wherein the reference value is 2.9 IU/L.)

The present invention will be described below in detail with reference to an embodiment.

Figure 1:
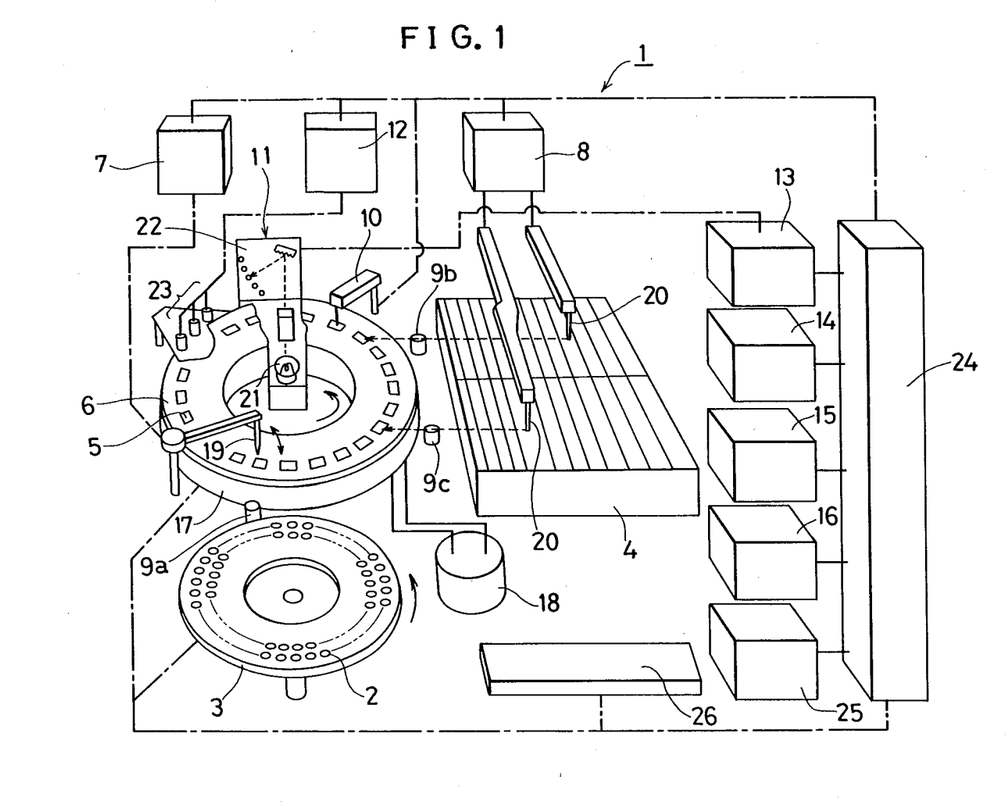
FIG. 1 is a diaphragm showing the construction of an automatic analyzer embodying the present invention.

With reference to FIG. 1, an automatic analyzer 1 consists essentially of sample containers 2, sample container moving means 3, reagent containers (not shown), a reagent container holding means 4, reaction containers 5, reaction container moving means 6, sample pouring means 7, reagent pouring means 8, three cleaning vessels 9a to 9c, stirring means 10, measuring means 11, cleaning means 12, an analog-digital converter 13, counting-calculating means 14, operation control means 15 ad display means 16.

The sample container moving means 3 comprises a horizontal turntable in the form of a disk. The sample containers 2 accommodating different blood samples individually are mounted on the upper surface of the turntable with their open ends up and are arranged at a predetermined spacing on two concentric circles centered about the axis of rotation of the turntable. The turntable is rotatable intermittently by one pitch of containers 2 at a time.

The reagent container holding means 4 comprises a rectangular tank having an open upper side. The reagent containers (not shown) containing a reagent, such as the one to be described later, for determining guanase activity are held in the tank with their open ends up. The holding means 4 is adapted to maintain the interior of the reagent containers at a predetermined low temperature.

The reaction container moving means 6 comprises a doughnut-shaped horizontal turntable. The reaction containers 5 are mounted on the upper surface of the turntable with their open ends up and are arranged at a predetermined spacing along a circle centered about the axis of rotation of the turntable. A temperature controlled bath 17 is attached to the lower side of the turntable for maintaining the interior of the reaction containers 5 at a constant temperature. The temperature controlled bath 17 is similar in shape to the moving means 6, has a channel-like cross section and has accommodated therein the lower portions of the reaction containers 5. Indicated at 18 is a fluid heater-feeder for the temperature controlled bath 17. The moving means 6 is intermittently rotatably by one pitch of containers 5 at a time.

The sample pouring means 7 has one pouring nozzle 19 which is reciprocatingly movable in a direction from the sample container moving means 3 toward the reaction container moving means 6 and in a direction opposite thereto for pouring a blood sample into each of the reaction containers 5. The reagent pouring means 8 has two pouring nozzles 20, 20 each movable from the reagent container holding means 4 toward the reaction container moving means 6 and in the opposite direction reciprocatingly for pouring the reagent into each of the reaction container 5.

The cleaning vessels 9a to 9c are each in the form of a container having an open upper end. The vessel 9a is disposed between the reaction container moving means 6 and the sample container moving means 3, while the vessels 9b and 9c are provided between the moving means 6 and the reagent container holding means 4. Each nozzle 19 or 20 is inserted into the cleaning vessel 9a, 9b or 9c every time the sample or reagent has been poured in, whereby the nozzle is cleaned.

The stirring means 10 is disposed in the vicinity of the outer periphery of the reaction container moving means 6 forwardly of the sample and reagent pouring positions in the direction of movement of the reaction containers 5. The mixture of reagent and sample placed into each reaction container and to be reacted is stirred by the means 10.

The measuring means 11 comprises a lamp 21, a photometer 22 and a filter (not shown) which are arranged forwardly of the stirring means 10 in the direction of movement of the reaction containers 5 and is adapted to colorimetrically measure the absorbance of each reaction mixture at a specified wavelength.

The cleaning means 12 comprises three cleaning nozzles 23 and is adapted to clean the interior of the reaction container 5 after the completion of the measurement, at a position forwardly of the measuring means 11 in the direction of movement of the reaction containers 5.

The analog-digital (A-D) converter 13 is electrically connected to the photometer 22. An analog signal delivered from the photometer 22 and representing a guanase measurement is converted to a digital signal by the converter.

The counting-calculating means 14 and the operation control means 15 are included in a microcomputer. The counting-calculating means 12 is electrically connected to the A-D converter 13 via an interface 24 to count and calculate the digital signal from the converter 13. The operation control means 15 is electrically connected, via the interface 24 to the sample container moving means 3, reaction container moving means 6, sample and reagent pouring means 7, 8, cleaning means 12 and stirring means 10 for controlling the operation of these six means.

The display means 16 comprises a printer and is electrically connected to the counting-calculating means 14 by way of the interface 24. The calculated value fed out from the means 12 is converted to a display signal, which is shown. When the display value is above the predetermined guanase activity value of 1.8 IU/L, the means 16 produces an exclusion signal for excluding the measured sample corresponding to the display value. The exclusion signal comprises an exclusion mark which is printed out along with the display value. The display means 16 may comprise a CRT in place of the printer. Indicated at 25 is a CRT serving as input means, and at 26 an operation panel.

Alternatively, the reaction container moving means, as well as the sample container moving means, may be adapted to move a row or rows of containers straight.

The operation of the analyzer 1 and the method of determining guanase activity with use of the analyzer will be described.

First, blood samples (serum or plasma samples) and reagents are placed into the reaction containers 5, and the mixture within each container 5 is stirred. The absorbance of the reaction mixture in each container 5 is measured, and the measurement is printed out. If the measurement is above the foregoing reference value, an exclusion signal is given to exclude the blood sample concerned. The analyzer 1 is usable not only for the determination of guanase activity but also for analyzing other items. The analyzer is serviceable also as one line of a multi-channel analyzer.

Normal blood samples (n=10) were checked by the preferred method of reaction rate assay (a) using the analyzer of the invention as will be described below.

(1) Procedure

To a single reagent system are added 360 μl of substrate buffer and 20 μl of sample, and the mixture is preincubated for 4 minutes. During the subsequent 5-minute period, the variation of absorbance is measured at two wavelengths of 546 nm and 700 nm. The activity value is given by the ratio of the sample to the standard guanase in the variation of absorbance per unit time, multiplied by the standard guanase activity.

The substrate buffer used is a mixture of the following reagents.

| Reagent | for 50 samples × 5 |
|---|---|
| Substrate solution (guanine, NaOH) | 10 ml × 5 |
| Buffer (NBT) | 10 ml × 5 |
| Color developing solution (1-mPMS) | 2.5 ml × 1 |
| Enzyme I (ASOD lyophilized) | for 20 ml × 5 |
| Enzyme II (XOD ammonium sulfate suspension) | 2.5 ml × 1 |

(2) Result of assay

| n | Guanase activity |
|---|---|
| 1 | 1.17 |
| 2 | 0.95 |
| 3 | 1.32 |
| 4 | 1.11 |
| 5 | 0.69 |
| 6 | 0.83 |
| 7 | 1.12 |
| 8 | 0.90 |
| 9 | 0.86 |
| 10 | 1.31 |
| $\bar{x}$ | 1.03 |
| SD | 0.212 |

On the other hand, blood samples were similarly checked by the preferred method of end point assay (b) using the present analyzer as will be described below.

(1) Procedure

65 μl sample

0.25 ml pretreatment buffer warming at 40° C. for 2 minutes.

0.50 ml substrate buffer warming at 40° C. for 12 minutes.

1.0 ml color developing solution warming at 40° C. for 2 minutes.

Measuring absorbance at main wavelength of 570 nm and sub-wavelength of 710 nm.

(2) Preparation of reagents (for 100 samples)

1. Pretreatment buffer

One vial of enzyme mixture I is dissolved in 25 ml of buffer I. The solution is usable for the following 5 days when stored in refrigerator.

2. Substrate buffer

Buffer II (45 ml) is added to 5 ml of guanine solution. If guanine separates out during storage, the solid can be dissolved by warming.

3. Color developing solution

Color developing solutions I and II are mixed together, each in an amount of 50 ml. One vial of peroxidase is dissolved in the mixture. The solution prepared should be shielded from light with aluminum foil.

4. Standard guanase solution

One vial of standard guanase is dissolved in 10 ml of purified water for use.

(3) Reagents (for 2000 samples)

1. Enzyme mixture:
Twenty vials, each for 100 samples.
2. Guanine solution:
Guanine alkali solution, 50 ml×2.
3. Buffer I:
Buffer for dissolving the enzyme mixture, 500 ml×1.
4. Buffer II:
Buffer for diluting the guanine solution, 500 ml×2.
5. Color developing solution I
Used as mixed with color developing solution II, in equal amounts, 500 ml×2.
6. Color developing solution II
Used as mixed with color developing solution I, in equal amounts, 500 ml×2.
7. Peroxidase:
Twenty vials, each for 100 samples.
8. Standard guanase:
Four vials, each for 500 samples.

(4) Result of assay

| n | Guanase activity |
|---|---|
| 1 | 1.25 |
| 2 | 1.46 |
| 3 | 1.45 |
| 4 | 0.85 |
| 5 | 1.46 |
| 6 | 1.25 |
| 7 | 1.29 |
| 8 | 1.03 |
| 9 | 1.34 |
| 10 | 2.37 |
| $\bar{x}$ | 1.38 |
| SD | 0.401 |

In either of the above method, no exclusion signal was emitted from the analyzer, indicating that the blood samples were all suited to transfusions.

Using the above analyser, the two methods were checked for correlation with the manual method of our prior invention (wherein the indophenol reaction is used) with the following results.

A. Reaction rate assay method (a)

(Reagent formulations)

1. Guanine solution: Guanine (12 mg) is dissolved in 25 ml of 12 mM of NaOH.
2. Enzyme preparation: Xanthine oxidase (400 U) and 180 mg of bovine serum alubmin are dissolved in 1 ml of distilled water, followed by lyophilization.
3. Buffer. NBT (231 mg) and 10 mg of mPMS are dissolved in 1 liter of 0.1M of tris maleate buffer.
4. Standard guanase: Purified guanase derived from rabbit is lyophilized.

(Preparation of reagents)

1. Substrate buffer (100 ml)
The buffer (97.5 ml) is thoroughly admixed with 2.5 ml of the guanine solution. One vial of the enzyme preparation is dissolved in the solution.

2. Standard guanase solution
One vial of the standard quanase is dissolved in 10 ml of pure water before use.

(Assay procedure)

Figure 2:
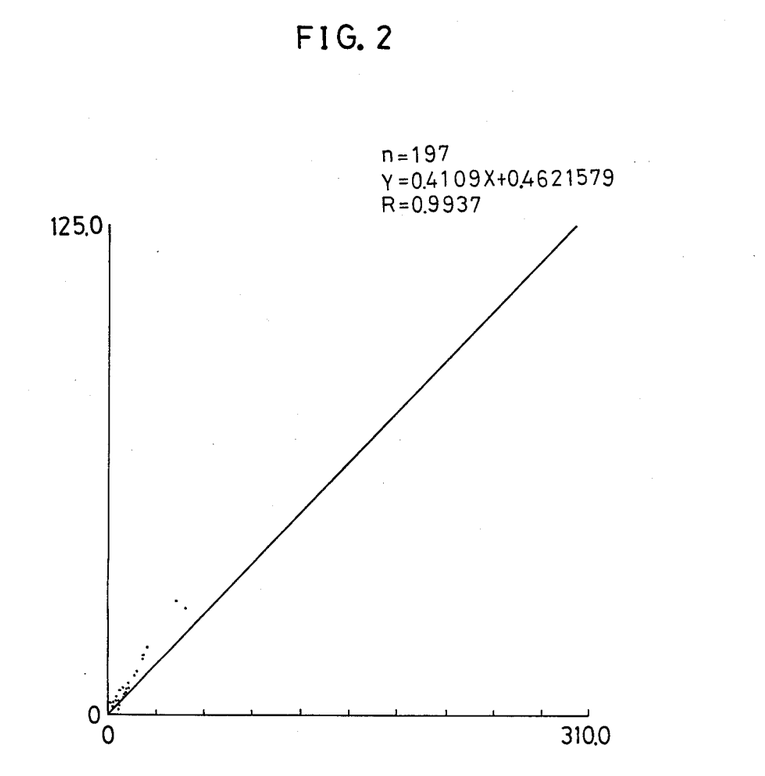
FIG. 2 is a graph showing the correlation between the guanase measurement obtained by a reaction rate assay according to the invention and the guanase measurement obtained by the manual method.

Using the present automatic analyzer, 20 μl of sample is admixed with 360 μl of the substrate buffer, the mixture is heated at 37° C. for 3 minutes, and the variation of absorbance is measured at main wavelength of 530 nm and sub-wavelength of 700 nm. FIG. 2 shows the result.

B. End point assay method (b)

1. Enzyme mixture (lyophilized)
Bovine serum albumin (150 g) is dissolved in 400 ml of 0.2M sodium hydroxide solution, and the solution is adjusted to a pH of 8.0 with 1N sodium hydroxide reagent. The following enzymes are dissolved, each in an amount corresponding to the enzymatic activity given, in the bovine serum albumin solution.

Uricase 9 IU, catalase 60 IU, super-oxide 2160 IU, xanthine oxidase 3.6 IU.

The solution is adjusted to a volume of 800 ml with purified water, and 10-ml portions of the solutions are placed into 50-ml vials and then lyophilized.

2. Guanine solution
Guanine (0.73 g) and 4.24 g of sodium azide are completely dissolved in a small amount of purified water containing 0.8 g of sodium hydroxide to obtain 2 liters of solution.

3. Buffer I
Potassium phosphate monobase (10.08 g), 161.6 g of potassium phosphate dibase and 5.0 ml of benzalkonium chloride solution are dissolved in purified water to obtain 20 liters of solution.

4. Buffer II
Potassium phosphate monobase (368 g), 303 g of potassium phosphate dibase and 10.0 ml of benzalkonium chloride solution are dissolved in purified water to obtain 20 liters of solution.

5. Color developing solution I
3-Methyl, 2-benzothiazolinonehydrazone hydrochloride (4.314 g), 222 g of citric acid and 126 g of disodium phosphate are dissolved in purified water. To the solution is added 10.0 ml of benzalkonium chloride solution to obtain 20 liters of solution with addition of purified water.

6. Color developing solution II
N,N-diethylaniline hydrochloride (222.8 g), 222 g of citric acid monohydrate and 126 g of disodium phosphate are dissolved in purified water. To the solution are added 10.0 ml of benzalkonium chloride solution and purified water to prepare 20 liters of solution.

7. Peroxidase
Bovine serum albumin (12 g) is dissolved in 300 ml of purified water, and the solution is adjusted to a pH of 8.0 with 1N sodium hydroxide reagent. To the solution are further added 2400 IU of peroxidase and purified water, giving 400 ml of solution. The solution is placed into 50-ml vials in an amount of 5 ml each and then lyophilized.

8. Standard guanase
Prepared from rabbit derived guanase.

(Preparation of reagents)

1. Pretreatment buffer:
One vial of the enzyme mixture is dissolved in 25 ml of buffer I. The solution is usable for the subsequent 5 days if stored in refrigerator.

2. Substrate buffer

Buffer II (45 ml) is added to 5 ml of the guanine solution. If guanine separates out during preservation, the solid can be dissolved by heating.

3. Color developing solution

Color developing solutions I and II are mixed together, each in an amount of 50 ml. One vial of the peroxidase is dissolved in the mixture. The solution prepared is to be shielded from light with aluminum foil or the like.

4. Standard guanase solution

One vial of the standard guanase is dissolved in 10 ml of purified water before use.

(Assay procedure)

Figure 3:
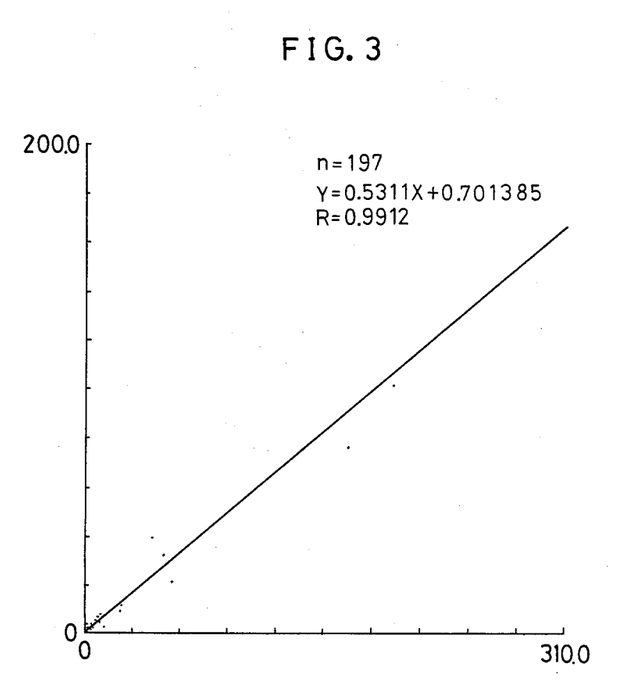
FIG. 3 is a graph showing the correlation between the guanase measurement obtained by an end point assay according to the invention and the guanase measurement obtained by the manual method.

Using the present automatic analyzer, 65 μl of sample is admixed with 0.25 ml of the pretreatment buffer, followed by heating at 40° C. for 2 minutes, addition of 0.50 ml of the substrate buffer and further heating at 40° C. for 12 minutes. With addition of 1.0 ml of the color developing solution, the sample mixture is heated at 40° C. for 2 minutes and then checked for variation of absorbance at main wavelength of 570 nm and subwavelength of 710 nm. FIG. 3 shows the result.

FIGS. 2 and 3 show that when either of the reaction rate assay method and the end point assay method is used for automatic analysis, a very good correlation was unexpectedly found between the method and the manual method, with a correlation coefficient r=0.9937 or r=0.9912 in either case. This indicates that the result of assaying guanase in the blood for transfusions by the automatic analysis method is reproducible, manifestly suggesting that the screening of blood by the present method is very effectively usable for preventing postoperative hepatitis, especially non-A non-B type hepatitis.

What is claimed is:

1. A blood screening automatic analyzer for determining guanase activity comprising a plurality of blood sample containers arranged in at least one row, each of said sample containers having an open end of accommodating different blood samples individually, a means for holding said sample containers with said open end facing upwardly and means for intermittently moving said sample containers along side at least one row, a plurality of reagent containers, each of said reagent containers having an open end for accommodating at least a reagent for an assay of a guanase activity of 1.8 IU/L, another means for holding each of said reagent containers with said open end facing upwardly and means for maintaining said reagent containers at a predetermined temperature, a plurality of reaction containers arranged in at least one row, each of said reaction containers having an open end, means for moving each of said reaction containers with said open end facing upwardly and means for intermittently moving said reaction containers along side at least one row, a temperature controlled bath for maintaining the reaction containers at a constant temperature, means for pouring a sample or reagent for an assay or a guanase activity of 1.8 IU/L into each of the reaction containers having a nozzle reciprocatingly moveable from the means for moving the sample container and the means for holding the reagent container towards the means for moving reaction container as well as in the opposite direction, cleaning vessels for cleaning the nozzle of the means for pouring after each pouring disposed between said means for moving the reactor container and the means for moving the sample container, means for stirring the mixture of sample and reagent to be reacted and poured into the reaction container at a position forwardly of a sample-reagent pouring position with respect to the movement of the reaction container moving means, means for measuring adapted to colorimetrically measure the absorbance of the reaction mixture and emit an analog measurement signal representing the measured absorbance at a position forwardly of the means for stirring with respect to the movement of the means for moving the reaction container, means for cleaning the reaction container after completion of the measurement at a position forwardly of the means for measuring with respect to the movement of the reaction container, an analog-digital converter electrically connected to said means for measuring for converting said measurement signal emitted from the means for measuring into a digital signal representing guanase activity, counting-calculating means for counting and calculating the digital signal, means for displaying showing the calculated value as converted to a display signal corresponding to a display value of a guanase activity of about 1.8 IU/L, and means for controlling the operation of the means for moving the reaction container, the means for pouring, the means for cleaning, and the means for stirring, said means for displaying being adapted to produce a signal for excluding the measured blood sample corresponding to a display value when the display value is above a guanase activity of 1.8 IU/L.

2. A method for determining guanase activity in a blood sample comprising:

(a) providing a blood screening automatic analyzer including a plurality of blood sample containers arranged in at least one row, each of said sample containers having an open end for accommodating different blood samples individually, means for holding said sample containers with said open end facing upwardly and means for intermittently moving said sample containers along side at least one row, a plurality of reagent containers, each of said reagent containers having an open end for accommodating a reagent, means for holding each of said reagent containers with said open end facing upwardly and means for maintaining said reagent containers at a predetermined temperature, a plurality of reaction containers arranged in at least one row, each of said reaction containers having an open end, means for moving each of said reaction containers with said open end facing upwardly and means for intermittently moving said reaction containers along side at least one row, a temperature controlled bath for maintaining the reaction containers at a constant temperature, means for pouring a sample or reagent into each of the reaction containers having a nozzle reciprocatingly moveable from the sample container moving means and the reagent container holding means towards the reaction container moving means as well as in the opposite direction, cleaning vessels for the cleaning the pouring nozzle of the sample-reagent pouring means after each pouring disposed between said reactor container moving means and the sample container moving means, means for stirring the mixture of sample and reagent to be reacted and poured into the reaction container at a position forwardly of a sample-reagent pouring position with respect to the movement of the reaction container moving means, measuring means adapted to colorimetrically measure the absorbance of the reaction mixture and emit an analog measurement signal representing the measured absorbance at a position forwardly of the stirring means with respect to the movement of the reaction container moving means, means for cleaning the reaction container after completion of the measurement at a position forwardly of the measuring means with respect to the movement of the reaction container, an analog-digital converter electrically connected to said measuring means for converting a said measurement signal emitted from the measuring means into a digital signal, counting-calculating means for counting and calculating the digital signal, display means for showing the calculated value as converted to a display signal, and means for controlling the operation of the reaction container moving means, the sample-reagent pouring means, the cleaning means, and the stirring means, said display means being adapted to produce a signal for excluding the measured blood sample corresponding to a display value when the display value is above a predetermined value;

(b) supplying a sample of blood to said blood sample containers;

(c) furnishing a reagent for an assay of a guanase activity of 1.8 IU/L;

(d) pouring a blood sample and reagent into said reaction containers and mixing said sample and said reagent together into a mixture;

(e) measuring colorimetrically the absorbance of said mixture;

(f) automatically converting the measurement of said absorbance into a digital signal representing guanase activity;

(g) calculating and converting said digital signal; and (h) showing the calculated value as converted to a display signal on a display means programmed to produce a signal for excluding the measured blood sample corresponding to a display value when the display value is above a guanase activity level of 1.8 IU/L.

3. An article of manufacture comprising a blood screening automatic analyzer for determining guanase activity including a plurality of blood sample containers arranged in at least one row, each of said sample containers having an open end for accommodating different blood samples individually, means for holding said sample containers with said open end facing upwardly and means for intermittently moving said sample containers along side at least one row, a plurality of reagent containers, each of said reagent containers having an open end and containing a reagent for an assay of a guanase activity of 1.8 IU/L, means for holding each of said reagent containers with said open end facing upwardly and means for maintaining said reagent containers at a predetermined temperature, a plurality of reaction containers arranged in at least one row, each of said reaction containers having an open end, means for moving each of said reaction containers with said open end facing upwardly and means for intermittently moving said reaction containers along side at least one row, a temperature controlled bath for maintaining the reaction containers at a constant temperature, means for pouring a blood sample or said reagent into each of the reaction containers having a nozzle reciprocatingly moveable from the sample container moving means and the reagent container holding means towards the reaction container moving means as well as in the opposite direction, cleaning vessels for the cleaning the pouring nozzle of the sample-reagent pouring means after each pouring disposed between said reactor container moving means and the sample container moving means, means for stirring the mixture of sample and reagent to be reacted and poured into the reaction container at a position forwardly of a sample-reagent pouring position with respect to the movement of the reaction container moving means, measuring means adapted to colorimetrically measure the absorbance of the reaction mixture and emit an analog measurement signal representing the measured absorbance at a position forwardly of the stirring means with respect to the movement of the reaction container moving means, means for cleaning the reaction container after completion of the measurement at a position forwardly of the measuring means with respect to the movement of the reaction container, an analog-digital converter electrically connected to said measuring means for converting a said measurement signal emitted from the measuring means into a digital signal representing guanase activity, counting-calculating means for counting and calculating the digital signal, display means for showing the calculated value as converted to a display signal corresponding to a display value of a guanase activity of about 1.8 IU/L, and means for controlling the operation of the reaction container moving means, the sample-reagent pouring means, the cleaning means, and the stirring means, said display means being adapted to produce a signal for excluding the measured blood sample corresponding to a display value when the display value is above a guanase activity of 1.8 IU/L.

* * * * *

UNITED STATES PATENT AND TRADEMARK OFFICE
CERTIFICATE OF CORRECTION

PATENT NO. : 4,788,141

DATED : November 29, 1988

INVENTOR(S) : YAMASAKI Seiichiro et al.

It is certified that error appears in the above-identified patent and that said Letters Patent is hereby corrected as shown below:

At column 1, line 11, change "samples for" to ---samples of blood---.

At column 1, line 24, change "enadngering" to ---endangering---.

At column 1, line 64, change "patent application" to ---Patent Application---.

At column 2, line 41, change "for" to ---to---.

At column 3, line 3, change "conventonal" to ---conventional---.

At column 4, line 18, change "diaphragm" to ---diagram---.

At column 6, line 27, change "ad" to ---and---.

At column 6, line 59, change "rotatably" to ---rotatable---. At column 7, line 3, change "container" to ---containers---. At column 9, line 58, change "alubmin" to ---albumin---.

Signed and Sealed this

Seventeenth Day of September, 1991

Attest:

HARRY F. MANBECK, JR.

*Attesting Officer*         *Commissioner of Patents and Trademarks*